(12) United States Patent
Harbige et al.

(10) Patent No.: US 10,576,086 B2
(45) Date of Patent: Mar. 3, 2020

(54) TRIAZINE DERIVATIVES AS INTERFERON-GAMMA INHIBITORS

(71) Applicant: University of Greenwich, London (GB)

(72) Inventors: Laurence Harbige, London (GB); Michael Leach, Kent (GB)

(73) Assignee: UNIVERSITY OF GREENWICH (GB)

( * ) Notice: Subject to any disclaimer, the term of this patent is extended or adjusted under 35 U.S.C. 154(b) by 0 days.

(21) Appl. No.: 15/735,852

(22) PCT Filed: Jun. 10, 2016

(86) PCT No.: PCT/GB2016/051711
§ 371 (c)(1),
(2) Date: Dec. 12, 2017

(87) PCT Pub. No.: WO2016/198878
PCT Pub. Date: Dec. 15, 2016

(65) Prior Publication Data
US 2018/0169105 A1    Jun. 21, 2018

(30) Foreign Application Priority Data

Jun. 12, 2015 (GB) .................................. 1510356.7
Mar. 15, 2016 (GB) .................................. 1604394.5

(51) Int. Cl.
*A61K 31/53*    (2006.01)

(52) U.S. Cl.
CPC .................................. *A61K 31/53* (2013.01)

(58) Field of Classification Search
CPC .................................................... A61K 31/53
See application file for complete search history.

(56) References Cited

U.S. PATENT DOCUMENTS

| | | | | |
|---|---|---|---|---|
| 5,712,277 A * | 1/1998 | Nakamura-Craig | ... | A61K 31/53 514/242 |
| 8,691,818 B2 * | 4/2014 | Leach | ................. | C07D 253/06 514/242 |
| 8,748,600 B2 * | 6/2014 | Leach | ................. | C07D 409/06 544/182 |
| 9,422,253 B2 * | 8/2016 | Leach | ................. | C07D 253/06 |
| 9,862,691 B2 * | 1/2018 | Leach | ................. | C07D 253/06 |
| 2004/0185049 A1 * | 9/2004 | Hunter | .................... | A61K 38/20 424/145.1 |
| 2013/0142809 A1 * | 6/2013 | Welcher | ................. | G01N 33/68 424/145.1 |

FOREIGN PATENT DOCUMENTS

| | | |
|---|---|---|
| EP | 0021121 A1 | 1/1981 |
| JP | 200095737 A | 4/2000 |
| WO | 2007146712 A2 | 12/2007 |
| WO | 2008007149 A2 | 1/2008 |
| WO | 2009090431 A1 | 7/2009 |
| WO | 2011004195 A2 | 1/2011 |
| WO | 2011004196 A1 | 1/2011 |

OTHER PUBLICATIONS

Chemical Abstracts Registry No. 1174184-38-3, indexed in the Registry file on STN CAS Online on Aug. 13, 2009. (Year: 2009).*
Doan et al., The Journal of Clinical Pharmacology, 2005, 45, pp. 751-762. (Year: 2005).*
International Search Report for PCT/GB2016/051711, dated Aug. 26, 2016.
Written Opinion for PCT/GB2016/051711, dated Aug. 26, 2016.

* cited by examiner

*Primary Examiner* — Laura L Stockton
(74) *Attorney, Agent, or Firm* — Heslin Rothenberg Farley & Mesiti, P.C.

(57) ABSTRACT

The present invention relates to interferon-gamma (IFN-γ) inhibitors, and their utility in treating or controlling diseases that can be treated or controlled through inhibition of IFN-γ production, such as Alzheimer's disease, prion diseases, multiple sclerosis, epilepsy, rheumatoid arthritis, inflammatory bowel disease, uveitis, autoimmune skin diseases, psoriasis, Sjögren's syndrome, Crohn's disease, and type 1 diabetes mellitus. The compounds are of Formula 1, 2 3, or are solvates, tautomers, or pharmaceutically acceptable salts thereof.

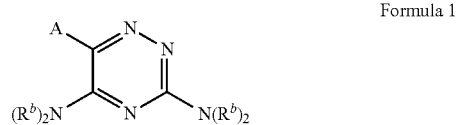

Formula 1

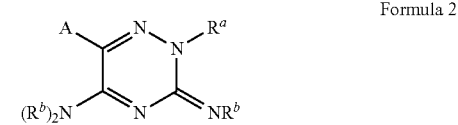

Formula 2

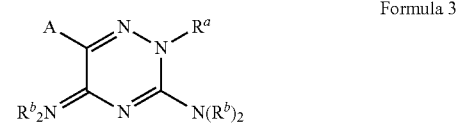

Formula 3

18 Claims, 3 Drawing Sheets

TRIAZINE DERIVATIVES AS INTERFERON-GAMMA INHIBITORS

CROSS REFERENCE TO RELATED APPLICATIONS

This application is a U.S. National Phase filing under 35 U.S.C. § 371 of International Application PCT/GB2016/051711, filed Jun. 10, 2016, and published as WO 2016/198878 A1 on Dec. 15, 2016. PCT/GB2016/051711 claims priority from Great Britain application numbers 1510356.7, filed Jun. 12, 2015, and 1604394.5, filed Mar. 15, 2016.

TECHNICAL FIELD

The present invention relates to triazine compounds that can be used to treat medical conditions that can be treated or controlled by inhibition of interferon gamma (IFN-γ).

BACKGROUND

IFN-γ is a cytokine that is involved in pathogenic immunity, and plays an important role in macrophage activation, and in the upregulation of class I and II major histocompatibility complex (MHC) antigens. It is produced by natural killer (NK) T cells, by CD4 T helper 1 ($T_h1$) cells, and also by CD8 cytotoxic T lymphocytes (CTL) effector T cells.

One of the crucial roles of IFN-γ is in immunomodulation and immunostimulation. Autoinflammatory and autoimmune conditions can be associated with overproduction or imbalances in IFN-γ secretion, whilst IFN-γ itself has been used to treat patients with immunodeficiencies such as chronic granulomatous disease. IFN-γ has, for example, been implicated in Alzheimer's disease and prion-related diseases (Bate et al; Journal of Neuroinflammation; 2006, 3:7, doi:10.1186/1742-2094-3-7), multiple sclerosis (Traugott et al; Annals of Neurology, 24(2), 1988, 243-251), and epilepsy (Sinha et al; Epilepsy Research, 2008, 82(2-3), 171-176).

A number of cyclic diazo and triazo compounds have been previously reported as being antifolates, and also voltage dependent sodium channel blockers, for example as described in WO 2008/007149, WO 2009/090431, WO 2011/004195 and WO 2011/004196. Disorders in mammals that are said to be treatable by sodium channel blocking include epilepsy, multiple sclerosis, glaucoma and uveitis, cerebral traumas and cerebral ischemias, stroke, head injury, spinal cord injury, surgical trauma, neurodegenerative disorders, motor neurone disease, Alzheimers disease, Parkinsons disease, chronic inflammatory pain, neuropathic pain, migraine, bipolar disorder, mood anxiety, cognitive disorders, schizophrenia and trigeminal autonomic cephalalgias. Antifolates can be used to treat mammalian cancers, and can also act as antimalarials against *Plasmodium vivax* and *Plasmodium falciparum* malaria, especially in humans.

There remains a need for compounds that can modulate the production of the pro-inflammatory cytokine IFN-γ, so that medical conditions and diseases that are related to its presence or over-production can be treated or controlled.

SUMMARY OF INVENTION

According to the present invention, there is provided a compound of Formula 1, Formula 2 or Formula 3 or a solvate, tautomer, or pharmaceutically acceptable salt thereof, for use in the treatment or control of medical conditions and diseases that are treatable or controllable by inhibiting interferon gamma (IFN-γ) production.

Formula 1

Formula 2

Formula 3

A is an aromatic ring selected from:
i. a phenyl ring substituted with up to five substituents, each independently selected from halogen atoms, haloalkyl groups having from 1 to 4 carbon atoms, alkoxy groups having from 1 to 4 carbon atoms, and haloalkoxy groups having from 1 to 4 carbon atoms;
ii. a thiophene ring optionally substituted with up to three substituents each selected independently from halogen atoms, alkyl groups having from 1 to 4 carbon atoms, haloalkyl groups having from 1 to 4 carbon atoms, alkoxy groups having from 1 to 4 carbon atoms and haloalkoxy groups having from 1 to 4 carbon atoms; and
iii. a $C(R^d)_3$ group, wherein each $R^d$ is independently selected from hydrogen, alkyl groups having from 1 to 4 carbon atoms, haloalkyl groups having from 1 to 4 carbon atoms, alkoxy groups having from 1 to 4 carbon atoms, haloalkoxy groups having from 1 to 4 carbon atoms, cycloalkyl groups having from 3 to 8 carbon atoms, halocycloalkyl groups having from 3 to 8 carbon atoms, and phenyl rings optionally substituted with up to five substituents, each independently selected from halogen atoms, alkyl groups having from 1 to 4 carbon atoms, haloalkyl groups having from 1 to 4 carbon atoms, alkoxy groups having from 1 to 4 carbon atoms, and haloalkoxy groups having from 1 to 4 carbon atoms, and wherein at least one $R^d$ is an optionally substituted phenyl ring.

$R^a$ is selected from hydrogen, haloalkyl groups having from 1 to 4 carbon atoms, and alkyl-alkoxy groups having from 1 to 6 carbon atoms that are optionally substituted with one or more halogen atoms, with the proviso that when A is a phenyl ring comprising one or more directly bound halogen substituents, the compound is of Formula 2 or Formula 3, and $R^a$ is not hydrogen.

Each $R^b$ is independently selected from hydrogen, and alkyl groups having from 1 to 4 carbon atoms, and haloalkyl groups having from 1 to 4 carbon atoms.

By "substituted" is meant that one or more of the hydrogen atoms on the phenyl or thiophene ring are replaced by any of the specified groups.

Conditions treatable or controllable through IFN-γ inhibition include Alzheimer's disease, prion diseases, multiple sclerosis and epilepsy. Other conditions include rheumatoid arthritis, inflammatory bowel disease, uveitis, autoimmune skin diseases, psoriasis, Sjögren's syndrome, Crohn's disease, and type 1 diabetes mellitus.

In another aspect, the invention relates to a compound of Formula 1, Formula 2 or Formula 3 as defined above, or a solvate, tautomer or pharmaceutically acceptable salt thereof, for use in treating or controlling Alzheimer's disease, prion diseases, multiple sclerosis, epilepsy, rheumatoid arthritis, inflammatory bowel disease, uveitis, autoimmune skin diseases, psoriasis, Sjögren's syndrome, Crohn's disease, and type 1 diabetes mellitus, where the compound inhibits the production of IFN-γ.

The invention also relates to a method of treating or controlling medical conditions and diseases that can be treated or controlled by inhibiting IFN-γ production. The method comprises administering to a patient a therapeutically effective amount of a compound of Formula 1, Formula 2 or Formula 3 as defined above, or a pharmaceutically acceptable salt thereof.

The invention further relates to the use of a compound according to Formula 1, Formula 2 or Formula 3 as defined above, for the manufacture of a pharmaceutical composition for the treatment or control of medical conditions and diseases that are treatable or controllable by inhibiting IFN-γ production.

The compounds are useful for treating mammals, especially humans.

BRIEF DESCRIPTION OF THE DRAWINGS

The present invention will now be described with reference to the accompanying drawings, in which.

DESCRIPTION OF EMBODIMENTS

Treatable Diseases and Medical Conditions

The compounds and salts of Formula 1, Formula 2 and Formula 3 can inhibit production of IFN-γ, and hence are suitable for treating diseases that are associated with the presence or over-production of excess IFN-γ.

IFN-γ has been shown to increase neuronal death in response to amyloid-$\beta_{1-42}$ (Bate et al; see above). Because amyloid-$\beta_{1-42}$ is linked to progression of Alzheimer's disease, and because IFN-γ-treated neurons became sensitised to the toxic effects of amyloid-$\beta_{1-42}$ and HuPrP82-146 (a neurotoxic peptide found in prion diseases), and had increased neuronal death rate, then IFN-γ inhibition can help to treat or control diseases such as Alzheimer's disease and prion-related diseases.

Prion-related diseases include transmissible spongiform encephalopathies (TSEs). Examples in human include Creutzfeldt-Jakob disease (CJD), new variant CJD (vCJD), Gerstmann-Sträussler-Scheinker syndrome (GSS), fatal familial insomnia, and multiple system atrophy (MSA). Examples in animals include bovine spongiform encephalopathy (BSE) and scrapie.

IFN-γ has also been linked to multiple sclerosis and epilepsy (Traugott et al; Sinha et al; see above).

IFN-γ is a representative marker of a $T_h1$ pro-inflammatory response. Therefore, by inhibiting IFN-γ the compounds can be used to treat $T_h1$ autoimmune and autoinflammatory diseases in which excessive $T_h1$-mediated responses are implicated. These include multiple sclerosis, rheumatoid arthritis, inflammatory bowel disease, uveitis, autoimmune skin diseases, psoriasis, Sjögren's syndrome, Crohn's disease and type 1 diabetes mellitus.

Pharmaceutically Acceptable Salts

The compounds of Formula 1, Formula 2 and Formula 3 can be provided in the form of pharmaceutically acceptable salts. Preferred salts are pharmaceutically acceptable acid addition salts. Suitable pharmaceutically acceptable acid addition salts include those formed with both organic and inorganic acids, for example from hydrochloric, sulphuric, citric, tartaric, phosphoric, lactic, pyruvic, acetic, malonic, succinic, oxalic, fumaric, maleic, oxaloacetic, methanesulphonic, p-toluenesulphonic, benzene-sulphonic, glutamic, naphthoic, and isethionic acids. Ethanesulfonate, malate, mandalate, benzoate, and salicylate salts are also suitable. The compound is typically selected from those of Formula 1 or Formula 2.

Group A

In the compounds of Formula 1, Formula 2 and Formula 3, group A can be an aromatic ring that is either a substituted phenyl ring or an optionally substituted thiophene ring.

In embodiments, the ring A contains one or more halogen, haloalkyl or haloalkoxy substituents. In further embodiments, all substituents on A are halogen, haloalkyl or haloalkoxy substituents, and in still further embodiments, all substituents on A are halogen or haloalkyl.

Where ring A is a phenyl ring, compounds of the invention can be represented by Formula 4, Formula 5 and Formula 6:

Formula 4

Formula 5

-continued

Formula 6

In these embodiments, n is an integer from 1 to 5, and each $R^c$ is independently selected from haloalkyl groups having from 1 to 4 carbon atoms, alkoxy groups having from 1 to 4 carbon atoms, and haloalkoxy groups having from 1 to 4 carbon atoms. $R^a$ and $R^b$ have the definitions provided above for Formulae 1, 2 and 3.

In embodiments, n is from 2 to 4, and is preferably 2.

In embodiments, the compounds are selected from those of Formula 4 of Formula 5.

In embodiments, at least one substituent is a haloalkyl or haloalkoxy. In further embodiments, all substituents are haloalkyl or haloalkoxy. In still further embodiments, all substituents are haloalkyl.

In embodiments, the haloalkyl, alkoxy or haloalkoxy substituents have 1 carbon atom. In further embodiments, at least one substituent is trifluoromethyl.

In embodiments, the total number of alkoxy and haloalkoxy substituents is no more than 3. In further embodiments, there are no alkoxy or haloalkoxy substituents.

Examples of ring A include:
2,5-bistrifluoromethylphenyl
3,5-bistrifluoromethylphenyl
3,4,5-trimethoxyphenyl
2-difluoromethoxyphenyl
2-trifluoromethoxyphenyl
2-(1,1,2,2-tetrafluoroethoxy)phenyl
3-(1,1,2,2-tetrafluoroethoxy)phenyl
2,5-bis(2,2,2-trifluoroethoxy)phenyl
3,5-bis(2,2,2-trifluoroethoxy)phenyl In a preferred embodiment phenyl ring A is 3,5-bis(trifluoromethyl)phenyl.

In alternative embodiments A is a phenyl ring and at least one $R^c$ is a halogen atom. In these embodiments, the compound is of Formula 5 or 6, and $R^a$ does not include hydrogen. In embodiments where at least one $R^c$ is a halogen atom, n can be from 1 to 3, or from 2 to 3, or n=2. In embodiments, the compound is of Formula 5.

In further embodiments, all occurrences of $R^c$ are halogen atoms. In such embodiments, n is typically from 1 to 3, and in a further embodiment n is 2. Where n=3, the halogen substituents are preferably at the 2-, 3- and 5-positions. Where n=2, the halogen substituents are preferably at the 2- and 3-positions. The 1-position represents the carbon atom of the phenyl ring that is bound directly to the triazine ring.

The halogen atom is typically selected (at each occurrence) from fluorine, chlorine and bromine. In embodiments, at least one $R^c$ is chlorine. In further embodiments, all $R^c$ are chlorine, and n is 2 or 3, preferably 2.

In embodiments, where n is 2 or more, and where $R^c$ has at least one halogen atom and at least one other substituent, the other substituent(s) have at least one halogen atom.

Examples of phenyl rings A having a halogen substituent include:
2,3,4-trifluorophenyl
2,3,4,5-tetrafluorophenyl
2,3,4,5,6-pentafluorophenyl
2,3-dichlorophenyl
2,5-dichlorophenyl
3,5-dichlorophenyl
2,6-dichlorophenyl
2,3,5-trichlorophenyl
2,3,6-trichlorophenyl
2-bromophenyl
3-bromophenyl
2-fluoro-3-chloro-5-trifluoromethylphenyl
2-chloro-4,5-difluorophenyl
2-chloro-3-trifluoromethylphenyl
3-chloro-5-trifluoromethylphenyl
5-chloro-2-trifluoromethylphenyl
2,3-dichloro-6-trifluoromethylphenyl In embodiments, phenyl ring A is a 2,3-dihalo-substituted phenyl or 2,3,5-trihalo-substituted phenyl, such as 2,3-dichlorophenyl or 2,3,5-trichlorophenyl.

When A is an optionally substituted thiophene ring, the thiophene ring can be bound to the triazine ring via the carbon atom at the 2- or 3-position, in which the sulphur atom represents the 1-position. Structures below are shown for Formula 7, Formula 8 and Formula 9 (substitution at the 2-position), and also for Formula 10, Formula 11 and Formula 12 (substitution at the 3-position).

Formula 7

Formula 8

Formula 9

Formula 10

Formula 11

Formula 12

Formula 15

In preferred embodiments, the thiophene ring is bound via the 2-carbon atom, as represented by Formulae 7, 8 and 9. In embodiments, the compound is selected from those of Formula 7 or 8.

In one embodiment, n can be 0. In other embodiments, n is an integer from 1 to 3.

When n>0, each $R^c$ is independently selected from halogen atoms, alkyl groups having from 1 to 4 carbon atoms, haloalkyl groups having from 1 to 4 carbon atoms, alkoxy groups having from 1 to 4 carbon atoms, and haloalkoxy groups having from 1 to 4 carbon atoms. $R^a$ and $R^b$ have the definitions provided above for Formulae 1, 2 and 3.

In some embodiments, all $R^c$ substituents are halogen atoms, typically selected from fluorine, chlorine and bromine. In further embodiments, at least one halogen $R^c$ substituent is chlorine, and in still further embodiments all halogen $R^c$ substituents are chlorine.

In embodiments, the total number of alkoxy and haloalkoxy substituents is no more than 2. In further embodiments, there are no alkoxy or haloalkoxy substituents.

Examples of A, when based on a thiophene ring, include:
5-chlorothienyl
2,5-dichlorothienyl
3,4,5-trichlorothienyl
3-bromothienyl
5-bromothienyl
4,5-dibromothienyl In a preferred embodiment, A is 3,4,5-trichlorothienyl.

In other embodiments, group A can be $C(R^d)_3$. Each $R^d$ is independently selected from hydrogen, alkyl groups having from 1 to 4 carbon atoms, haloalkyl groups having from 1 to 4 carbon atoms, alkoxy groups having from 1 to 4 carbon atoms, haloalkoxy groups having from 1 to 4 carbon atoms, cycloalkyl groups having from 3 to 8 carbon atoms, halocycloalkyl groups having from 3 to 8 carbon atoms, and optionally substituted phenyl rings.

This embodiment is represented by Formula 13, Formula 14 and Formula 15 below.

Formula 13

Formula 14

In this formula n can be 0, or can be an integer in the range of from 1 to 5.

The optional $R^c$ substituents in this case are each independently selected from halogen atoms, alkyl groups having from 1 to 4 carbon atoms, haloalkyl groups having from 1 to 4 carbon atoms, alkoxy groups having from 1 to 4 carbon atoms, and haloalkoxy groups having from 1 to 4 carbon atoms.

In embodiments, at least one $R^d$ is an unsubstituted phenyl ring. In further embodiments, at least one $R^d$ is hydrogen. In yet further embodiments, at least one $R^d$ is a substituted phenyl ring, and at least one or all $R^c$ substituents are independently selected from alkyl groups and alkoxy groups. In yet further embodiments, two $R^d$ are optionally substituted phenyl rings.

In embodiments, the compound is of Formula 13 or 14.

Examples of compounds falling within the scope of Formulae 13, 14 and 15 include:

3,5-Diamino-6-(diphenylmethyl)-1,2,4-triazine [CEN-130]
3,5-Diamino-6-(1,1-diphenylethyl)-1,2,4-triazine [CEN-147]
5(3)-Amino-6-(1,1-diphenylethyl)-2,3(2,5)-dihydro-3(5)-imino-2-methyl-1,2,4-triazine [CEN-149]
3,5-Diamino-6-(triphenylmethyl)-1,2,4-triazine [R3=R4=R5=Ph] [CEN-153]
3,5-Diamino-6-(1-cyclopentyl-1-phenylmethyl)-1,2,4-triazine [CEN-163]
3,5-Diamino-6-(1-isopropyl-1-phenylmethy)-1,2,4-triazine [CEN-201]
3,5-Diamino-6-[1,1 bis-(4-chlorophenyl)methyl]-1,2,4-triazine [CEN-213].

Group $R^a$ $R^a$ is a substituent on the nitrogen at the 2-position of the 1,2,4-triazine ring in Formulae 2 and 3 above (and corresponding Formulae 5, 6, 8, 9, 11, 12, 14 and 15).

$R^a$ is selected from hydrogen, haloalkyl groups having from 1 to 4 carbon atoms, and alkyl-alkoxy groups having from 1 to 6 carbon atoms that are optionally substituted with one or more halogen atoms.

When A is a phenyl ring without directly bound halogen substituents, or a substituted thiophene ring, the compound is preferably either of Formula 1, i.e. $R^a$ is not present, or the compound is of Formula 2 or Formula 3 and $R^a$ is preferably hydrogen.

When A is a phenyl ring with at least one directly bound halogen substituent, $R^a$ is present, but is not hydrogen. In this embodiment, $R^a$ is preferably a haloalkyl group or an alkoxy-substituted alkyl group, in which the alkyl or alkoxy group optionally comprises at least one halogen substituent.

In preferred embodiments, $R^a$ is a haloalkyl group having from 1 to 4 carbon atoms, for example 2 to 3 carbon atoms. In further embodiments, $R^a$ comprises a trihalomethyl group. In still further embodiments, the carbon atom adjacent to the triazine nitrogen is unsubstituted.

Examples of $R^a$ when A is halogen-substituted phenyl include:
2,2-difluoroethyl
2,2-dichloroethyl
2,2-dibromoethyl
2,2,2-trifluoroethyl
2,2,2-trichloroethyl
2,2,2-tribromoethyl
3,3-difluoropropyl
2,2,3,3-tetrafluoropropyl
2,2,3,3,3-pentafluoropropyl In a preferred embodiment, $R^a$ is 2,2,2-trihaloethyl, for example 2,2,2-trichloroethyl.

Group $R^b$

This is a substituent group on the amino or imine groups at positions 3 or 5 of the triazine ring.

Each $R^b$ is independently selected from either hydrogen or alkyl groups having from 1 to 4 carbon atoms that are optionally substituted by one or more halogen atoms. In embodiments, the alkyl groups are unsubstituted.

In preferred embodiments, at least one $R^b$ on each nitrogen is hydrogen. In most preferred embodiments, all occurrences of $R^b$ are hydrogen.

Pharmaceutical Compositions

The compounds of Formula 1, Formula 2 or Formula 3, or pharmaceutically acceptable salts, thereof, can be included in a pharmaceutical composition.

The compounds are present in a therapeutically effective amount, i.e. an amount that is sufficient to be effective against the disorder in vivo.

The pharmaceutical composition can comprise pharmaceutically acceptable carriers, which can be used to prepare the compound according to Formula 1, Formula 2 or Formula 3 in a form suitable for administration to a patient, but without destroying the pharmaceutically beneficial effects of the compound.

In embodiments, the pharmaceutical composition may be given orally, parenterally, topically, or as a suppository.

It can be delivered to a patient, for example, by intradermal, intramuscular, intraperitoneal, intraveneous, subcutaneous, intranasal, or oral routes, for example. They can be administered by any convenient means, for example by infusion or bolus injection, or by absorption through epithelial or mucotaneous linings (e.g. oral, stomach, rectal or intestinal mucosa).

For oral administration, the pharmaceutical composition can be formulated into solid or liquid preparations, such as pills, tablets, troches, capsules, powder, granules, syrups, solutions, suspensions or emulsions.

Where used, fine powders or granules can contain diluting, dispersing and/or surface active agents. Where desirable or necessary, flavouring, preserving, suspending, or thickening agents can be included. They can be formulated in a dry form. For example, dry powders or granules may be provided in a sachet, contained in a capsule, or compressed to form a tablet. They may alternatively be formulated as a syrup, as a draught, or as an aqueous or non-aqueous suspension. Suspending agents may be included.

Other additives and excipients which may be included are, for example, medically inert ingredients, e.g., solid and liquid diluents such as lactose, starch, or calcium phosphate for tablet or capsules; olive oil or ethyl oleate for soft capsules; water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

The pharmaceutical compositions may be prepared by the admixture of a compound of Formula 1, Formula 2 or Formula 3 with a pharmaceutically acceptable carrier. Conventional pharmaceutical excipients may be admixed as required. Examples of suitable formulations are described in U.S. Pat. No. 4,649,139.

For injection, the compounds may be presented in sterile aqueous injection solutions, which include for example water, saline, dextrose, water-miscible solvents such as ethanol, polyethylene glycol and propylene glycol, and non-aqueous vehicles such as plant or animal oils. Optionally, the pH is in the range of from 6 to 8, for example 6.5 to 7.5. Optionally, buffers such as citrates, acetates or phosphates, can be present. Optionally, antioxidants such as ascorbic acid or sodium bisulphite can be present. Optionally, solubilising agents and stabilisers such as cyclodextrin, lysolecithin, oleic acid, stearic acid, and dextrin can be present. Optionally, local anaesthetics such as lignocaine and procaine hydrochloridecan can be present. Formulations such as those described in US 2004/0029934, comprising phosphatidylcholine and phosphatidylethanolamine, and those described in US 2004/0053888 comprising cyclodextrin, can be used.

The pharmaceutical composition can be provided in discrete units, which may conveniently contain an amount of compound of Formula 1, Formula 2 or Formula 3, which is effective at such dosage or as a multiple of the same. Typically, individual dosage units (e.g. each tablet, pill, sachet or 5 ml dose of liquid), contain in the range of from 5 mg to 500 mg of the compound or pharmaceutically acceptable salt thereof, for example in the range of from 2 mg to 250 mg. Examples of individual dosages include 2 mg, 5 mg, 25 mg, 50 mg, 100 mg and 200 mg of compound or pharmaceutically acceptable salt thereof.

The compound or salt thereof can be provided in one dose, or more than one dose, for example in the range of from two to eight doses per day, for example from two to four or from two to three doses per day.

Combinations

The compounds or salts can be administered in combination with one or more further compounds active for the same or for a different disorder.

Administration can be simultaneous, sequential or separate. The active ingredients can be combined into a single dosage, or they can be provided in the form of a kit comprising the two or more active ingredients in separate dosages.

Synthesis

Triazine compounds according to Formula 1, Formula 2 and Formula 3 can be prepared using the methods described in WO 2008/007149, WO 2009/090431, WO 2011/004195 and WO 2011/004196, in EP 0 021 121, and in U.S. Pat. No. 4,649,139.

Example Compounds

Examples of compounds having A=halogen-substituted phenyl, and falling within the definition of Formula 5 or Formula 6 include:

5(3)-amino-6-(2,3-dichlorophenyl)-2,3(2,5)-dihydro-3(5)-imino-2-(2-fluoroethyl)-1,2,4-triazine 5(3)-amino-6-(2,3-dichlorophenyl)-2,3(2,5)-dihydro-3(5)-imino-2-(2,2-difluoroethyl)-1,2,4-triazine 5(3)-amino-6-(2,3-dichlorophenyl)-2,3(2,5)-dihydro-3(5)-imino-2-(2,2,2-trifluoroethyl)-1,2,4-triazine [CEN-067]

5-amino-6-(2,3-dichlorophenyl)-2,3-dihydro-3-imino-2-(3,3,3-trifluoropropyl)-1,2,4-triazine 5(3)-Amino-6-(2,3-dichlorophenyl)-2,3(2,5)-dihydro-3(5)-imino-2-(2,2,3,3-tetrafluoropropyl)-1,2,4-triazine [CEN-218]

5(3)-Amino-6-(2,3-dichlorophenyl)-2,3(2,5)-dihydro-3(5)-imino-2-(2,2,3,3,3-pentafluoropropyl)-1,2,4-triazine [CEN-217]

5(3)-Amino-6-(2,3-dichlorophenyl)-2,3(2,5)-dihydro-3(5)-imino-2-(2,2,2-trichloroethyl)-1,2,4-triazine [CEN-216]

5(3)-amino-6-(2,3,-dichlorophenyl)-2,3(2,5)-dihydro-3(5)-imino-2-(2-isopropoxy)ethyl-1,2,4-triazine [CEN-091]

5(3)-amino-6-(2,3,5-trichlorophenyl)-2,3(2,5)-dihydro-3(5)-imino-2-(2-fluoroethyl)-1,2,4-triazine 5(3)-amino-6-(2,3,5-trichlorophenyl)-2,3(2,5)-dihydro-3(5)-imino-2-(2,2-difluoroethyl)-1,2,4-triazine [CEN-085]

5(3)-amino-6-(2,3,5-trichlorophenyl)-2,3(2,5)-dihydro-3(5)-imino-2-(3,3,3-trifluoropropyl)-1,2,4-triazine 5(3)-amino-6-(2,3,5-trichlorophenyl)-2,3(2,5)-dihydro-3(5)-imino-2-(2,2,2-trichloroethyl)-1,2,4-triazine [CEN-248]

5(3)-Amino-6-(3-chloro-2-fluoro-5-trifluoromethyphenyl)-2,3(2,5)-dihydro-3(5)-imino-2-(2,2,3,3-tetrafluoropropyl)-1,2,4-triazine [CEN-210]

5(3)-Amino-6-(3-chloro-2-fluoro-5-trifluoromethyphenyl)-2,3(2,5)-dihydro-3(5)-imino-2-(2,2,3,3,3-pentafluoropropyl)-1,2,4-triazine [CEN-211]

Preferred compounds have haloalkyl as the $R^a$ substituent. Most preferably, the compound is 5(3)-Amino-6-(2,3-dichlorophenyl)-2,3(2,5)-dihydro-3(5)-imino-2-(2,2,2-trichloroethyl)-1,2,4-triazine [CEN-216]. It can be provided, for example, as a trifluoromethanesulphonic acid salt.

Examples of compounds having A=phenyl with no directly attached halogen, and falling within the definition of Formulae 4, 5 and 6 include:

3,5-diamino-6-(2,5-bistrifluoromethylphenyl)-1,2,4-triazine [CEN-198]

3,5-diamino-6-(3,5-bistrifluoromethylphenyl)-1,2,4-triazine [CEN-092]

3,5-diamino-6-(3,4-dimethoxyphenyl)-1,2,4-triazine [CEN-115]

3,5-diamino-6-(3,5-dimethoxyphenyl)-1,2,4-triazine [CEN-192]

3,5-diamino-6-(3,4,5-trimethoxyphenyl)-1,2,4-triazine [CEN-095]

3,5-diamino-6-(2-difluoromethoxyphenyl)-1,2,4-triazine [CEN-142]

3,5-diamino-6-(2-trifluoromethoxyphenyl)-1,2,4-triazine [CEN-056]

3,5-diamino-6-[3-(1,1,2,2-tetrafluoroethoxy)phenyl]-1,2,4-triazine [CEN-108]

3,5-diamino-6-[2-(1,1,2,2-tetrafluoroethoxy)phenyl]-1,2,4-triazine [CEN-137]

3,5-diamino-6-[2,5-bis(2,2,2-trifluoroethoxy)phenyl]-1,2,4-triazine [CEN-140]

3,5-diamino-6-[3,5-bis(2,2,2-trifluoroethoxy)phenyl]-1,2,4-triazine [CEN-193]

Preferred compounds have one or more $R^c$ haloalkyl substituents on the phenyl ring. Preferably all $R^c$ substituents are haloalkyl. A preferred compound is 3,5-diamino-6-(3,5-bistrifluoromethylphenyl)-1,2,4-triazine [CEN-092].

Examples of compounds where A is a thiophene ring (thienyl), and falling within the definition of Formula 7, Formula 8 and Formula 9 include:

3,5-diamino-6-[2-(5-chlorothienyl)]-1,2,4-triazine [CEN-138]

3,5-diamino-6-[3-(2,5-dichlorothienyl)]-1,2,4-triazine [CEN-071]

3,5-diamino-6-[2-(3,4,5-trichlorothienyl)]-1,2,4-triazine [CEN-079]

3,5-diamino-6-[2-(5-bromothienyl)]-1,2,4-triazine [CEN-124]

3,5-diamino-6-[2-(3-bromothienyl)]-1,2,4-triazine [CEN-125]

3,5-diamino-6-[2-(4,5-dibromothienyl)]-1,2,4-triazine [CEN-122]

Preferred compounds include those where the thienyl group comprises at least one halogen $R^c$ substituent. Preferably, all substituents on the thienyl group are halogen. A preferred compound is 3,5-diamino-6-[2-(3,4,5-trichlorothienyl)]-1,2,4-triazine [CEN-079].

Solvates

The compounds of Formula 1, 2 or 3 can incorporate solvate molecules, for example originating from the solvent in which they are prepared. If prepared in aqueous media, for example, they can be prepared in the form of hydrates.

Tautomers

The compounds of Formula 1, 2 and 3 above can exist as tautomers.

For example, where the compound is of Formula 1, and at least one of the $R^b$ substituents on a nitrogen at the 3- or 5-position of the triazine ring is a hydrogen atom, the following tautomers can potentially arise:

Tautomeric forms of the compounds of Formulae 1, 2 and 3 are, therefore, also within the scope of the invention.

Rotamers

Depend on the nature of the groups and substituents on group A, and also on the groups on triazine ring, there may be restricted rotation about the bond between, for example, the triazine ring and group A, which can potentially give rise to different rotameric forms/isomers, which are also potentially separable.

All rotameric forms of the compounds of Formulae 1, 2 and 3 are, therefore, also within the scope of the invention.

EXPERIMENTAL

The ex vivo activity of various compounds towards suppression of IFN-γ production in human peripheral blood mononuclear cells (PBMCs) was studied.

Experiment 1

Blood samples (40-50 ml) were taken from five healthy volunteer Caucasian subjects (4 male, 1 female) aged between 20 and 40 years. They were not taking any other prescribed medication that could interfere with the results.

The blood was transferred into 50 ml centrifuge tubes (Corning, USA) containing heparin sodium salt 37.5 mg heparin powder diluted in 300-500 μl phosphate buffered saline (PBS) for 50 ml blood), and centrifuged at 2000 rpm for 10 minutes, and the plasma portion was separated. The plasma was further centrifuged at 3000 rpm for 10 minutes, and the supernatant separated and kept for later use.

The blood cells from the initial centrifugation were diluted with an equal volume of RPMI-1640 (Sigma, UK), and layered (2:1) onto Lymphoprep (Axis-Shield, Norway) in 25 ml universal tubes (Bibby Sterilin, UK) for density gradient centrifugation at 2500 rpm for 30 minutes.

PBMCs (lymphocytes and monocytes) were then removed from the interface, diluted in an equal volume of RPMI-1640 and washed twice by centrifugation at 3000 rpm for 10 minutes.

For testing, the PBMCs were re-suspended in a known volume of culture medium containing RPMI-1640 supplemented with 2 mM L-glutamine, 100 U penicillin, and 100 μg streptomycin (Sigma, UK).

The cell count was determined by the use of a haemocytometer using 10 μl of the cell suspension. The number of cells was determined based on a count in 5 random 1 mm squares.

The cell solution was then diluted with the supplemented RPMI-1640 medium to ensure a cell count of $2 \times 10^6$ cells/ml.

Cell viability was checked using trypan blue exclusion, using 0.04% trypan blue solution (0.4% trypan blue solution (Sigma, UK) diluted 10× with PBS). 10 μl trypan blue solution was mixed with 10 μl cell suspension, and after 5 minutes was mounted onto the haemocytometer. The total number of cells, and the total number of viable (colourless) cells were counted in three 1 mm squares. Viability was greater than 85% in all cases.

The PBMC suspension was added to tissue culture tubes (Bibby Sterilin, UK) with 5% autologous plasma, 5 μg/ml-phytohaemaglutinin (PHA) to stimulate T-lymphocyte IFN-γ production, and a solution containing various concentrations of the compound to be studied. A control containing no compound was also cultured for each subject.

In this experiment, the compounds used were lamotrigine (3,5-diamino-6-(2,3-dichlorophenyl)-1,2,4-triazine) and sipatrigine (4-amino-2-(4-methyl-1-piperazinyl)-(2,3,5-trichlorophenyl)-pyrimidine. Their structures are as follows:

Lamotrigine

Sipatrigine

Experiments using these compounds are comparative, as they do not fall within the scope of Formula 1, Formula 2 or Formula 3.

In the case of lamotrigine, the isethionate salt was used, and diluted with RPMI-1640 to produce 100 μM, 30 μM, 10 μM and 3 μM solutions that were tested on PBMCs from the first three subjects. With PBMC's from the other two subjects, a 300 μM solution was also tested.

For sipatrigine, the mesylate salt was used, and diluted with RPMI-1640 to produce 30 μM, 10 μM, 3 μM and 1 μM solutions. It was tested on PBMCs from the first three subjects only.

The tubes were incubated at 37° C. for 24 hours under a 5% $CO_2$ atmosphere. After incubation, the cells (>75% viable according to trypan blue test) were centrifuged at 3000 prm for 10 minutes, and the cell-free supernatants were collected and stored at −70° C. before analysis for IFN-γ.

Levels of IFN-γ produced by the PBMCs were determined by the DuoSet ELISA Development system for human IFN-γ (RD Systems, UK), with a sensitivity of 15.6-1000 pg/ml.

Capture antibody, detection antibody, standard and streptavidin-HRP (streptavidin conjugated to horseradish peroxidase) were provided. A 96-well microtitre plate (Corning CoStar, flat bottom, polystyrene, high binding microtitre plate, UK) was coated with 100 μl per well of capture antibody (mouse anti-human IFN-γ at 4.0 μg/ml), sealed and incubated overnight. Unbound capture antibody was washed from the wells three times, using a wash buffer (0.05% Tween 20 in PBS). Block buffer (1% bovine serum albumin (BSA) in PBS) was then added. After incubation for 1 hour, the wells were washed, and sample culture supernatants or standards were added. A 7-point standard curve (in the range 15.6-1000 pg/ml) was produced from 120 ng/ml recombinant human IFN-γ using 2-fold serial dilutions in reagent diluent (0.1% BSA, 0.05% Tween 20 in tris-buffered saline (20 mM Trizma base, 150 mM NaCl)). The sealed plates were left to incubate for 2 hours.

After further washing, the detection antibody (biotinylated goat anti-human IFN-γ at 175 ng/ml) was added, and the plates sealed and incubated for a further 2 hours. After washing, streptavidin-HRP was added to the wells and the covered plate was incubated for 20 minutes, out of direct light. The wells were washed again, the substrate solution (1:1 mixture of colour reagents A ($H_2O_2$) and B (TMB, tetramethylbenzidine)) was added, and the plates incubated for another 20 minutes, out of direct light. Stop solution (sulfuric acid) was added to halt the reaction, and the absorbance at 450 nm was measured by a microtitre plate reader (Thermo Labsystems Multiscan EX).

If the absorbance values were found to be above the highest standard value of 1000 pg/ml, the supernatant was diluted with RPMI-1640. The ELISA was then repeated, and results adjusted according to the dilution factor.

The absorbance/IFN-γ concentration relationship was determined from the linear best fit from the standards data.

The paired Student's t-test was used for comparison of control and test values, where P<0.05 was considered to be statistically significant.

Table 1 shows the effects of the compounds on IFN-γ production in the various subjects compared to the control.

TABLE 1

Effects of Comparative Compounds on IFN-γ Production by PBMCs

| | IFN-γ Concentration (pg/ml) | | | | | | | |
|---|---|---|---|---|---|---|---|---|
| Compound | Subject 1 | Subject 2 | Subject 3 | Subject 4 | Subject 6 | Mean | SD | SEM |
| Lamotrigine | | | | | | | | |
| 3 μM | 1153.13 | 1238.68 | 1641.69 | 937.30 | 1305.54 | 1255.27 | 256.74 | 114.82 |
| 10 μM | 923.32 | 1307.46 | 1180.21 | 895.04 | 1227.25 | 1106.66 | 186.19 | 83.27 |
| 30 μM | 872.99 | 1089.69 | 897.48 | 853.66 | 1191.37 | 981.04 | 150.77 | 67.43 |
| 100 μM | 834.21 | 886.41 | 392.96 | 775.28 | 1095.88 | 796.95 | 256.14 | 114.55 |
| 300 μM | | | | 495.48 | 798.32 | 646.90 | 214.14 | 151.42 |
| Control | 1055.84 | 1380.71 | 1594.64 | 994.00 | 1488.19 | 1302.68 | 265.5 | 118.73 |
| Sipatrigine | | | | | | | | |
| 1 μM | | | | | | 1275.07 | 105.61 | 60.97 |
| 3 μM | | | | | | 1227.27 | 437.21 | 252.43 |
| 10 μM | | | | | | 1331.70 | 281.57 | 162.57 |
| 30 μM | | | | | | 892.89 | 192.31 | 111.03 |
| Control | | | | | | 1343.73 | 271.30 | 156.63 |

Figure 1:
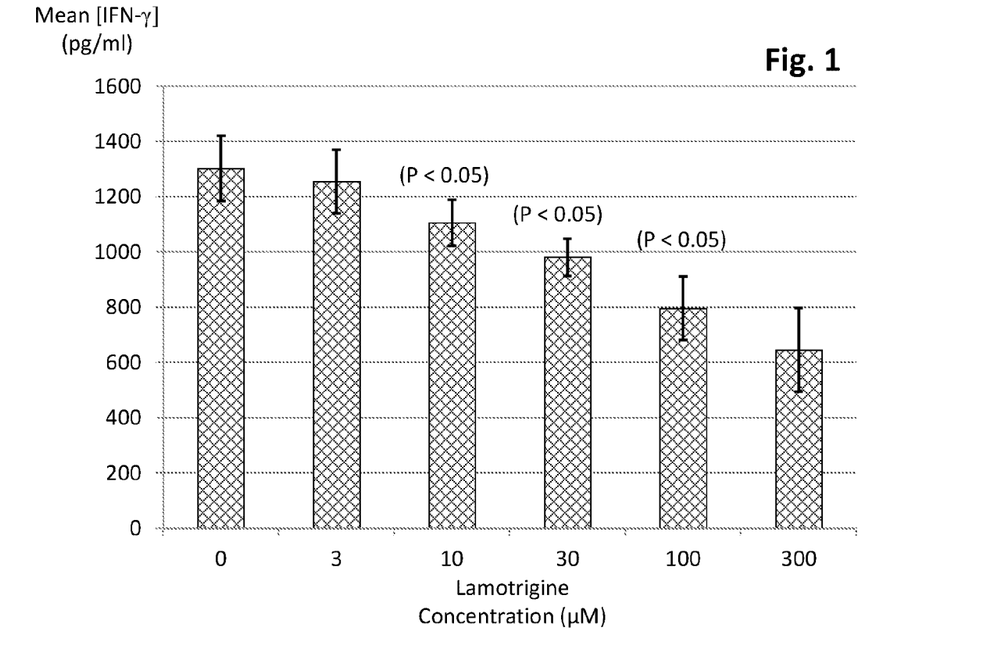
FIG. 1 is a chart showing the effects of lamotrigine on IFN-γ production in human peripheral blood mononuclear cells (PBMCs), based on the mean concentrations from Experiment 1.
Figure 2:
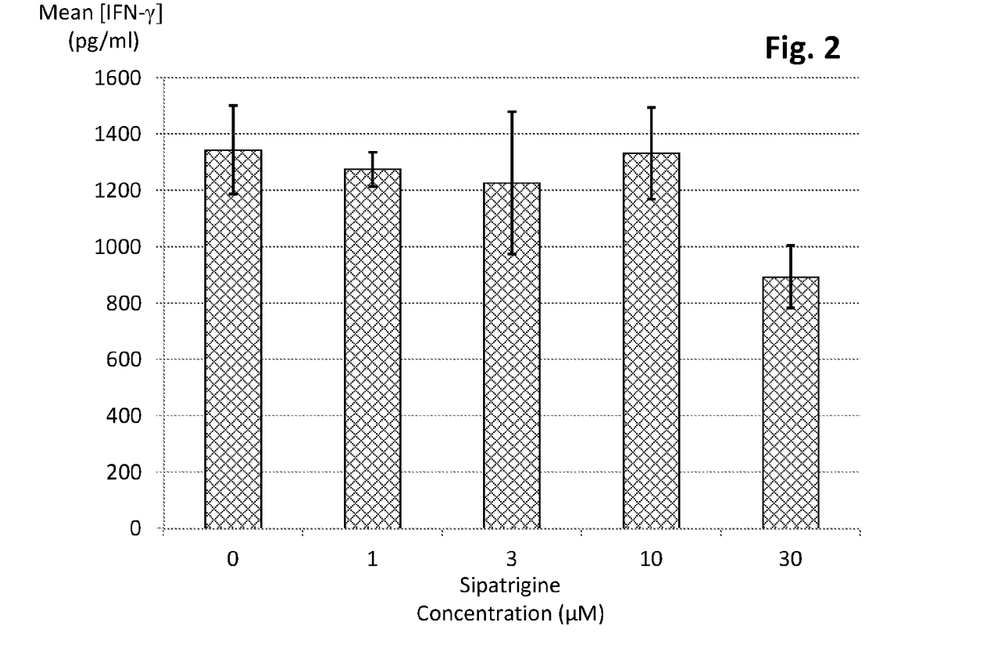
FIG. 2 is a chart showing the effects of sipatrigine on IFN-γ production in human peripheral blood mononuclear cells (PBMCs), based on the mean concentrations from Experiment 1.
Figure 3:
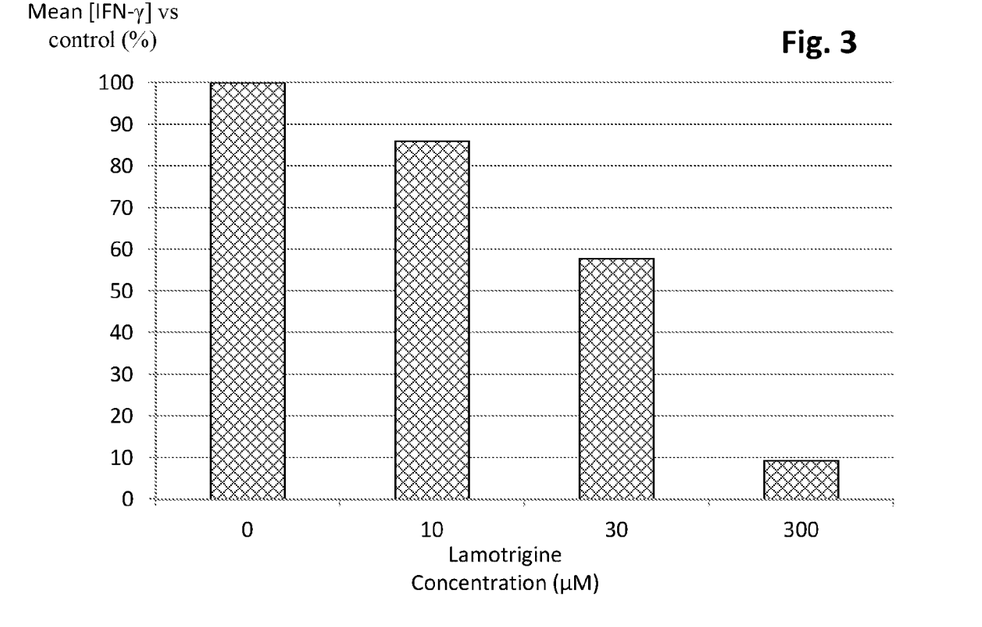
FIG. 3 is a chart showing the effects of lamotrigine on IFN-γ production in human peripheral blood mononuclear cells (PBMCs) based on the mean concentrations from Experiment 2.
Figure 4:
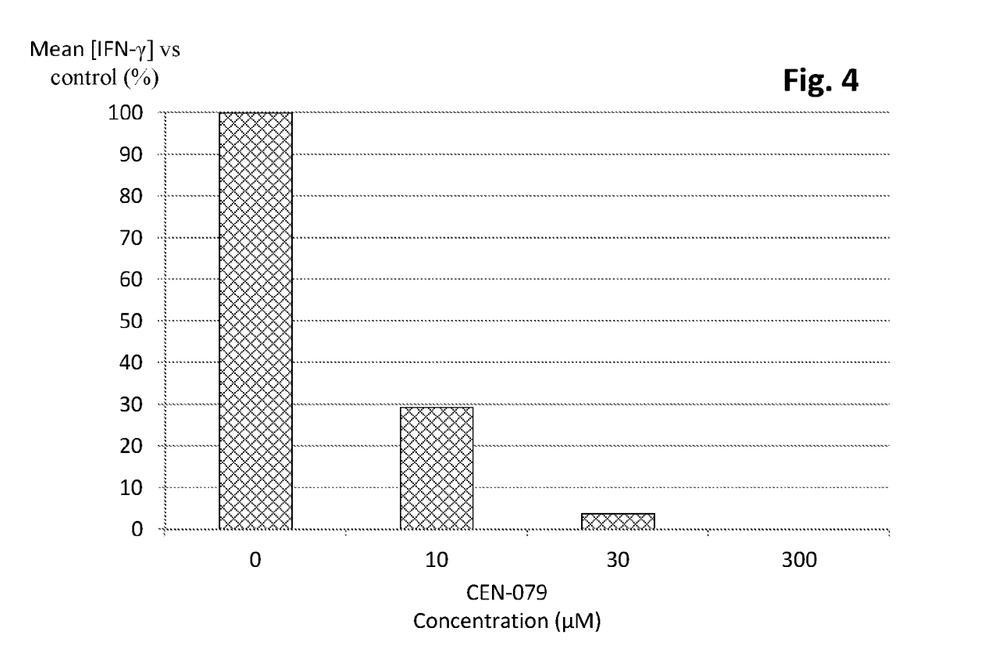
FIG. 4 is a chart showing the effects of compound CEN-079 on IFN-γ production in human peripheral blood mononuclear cells (PBMCs) based on the mean concentrations from Experiment 2.
Figure 5:
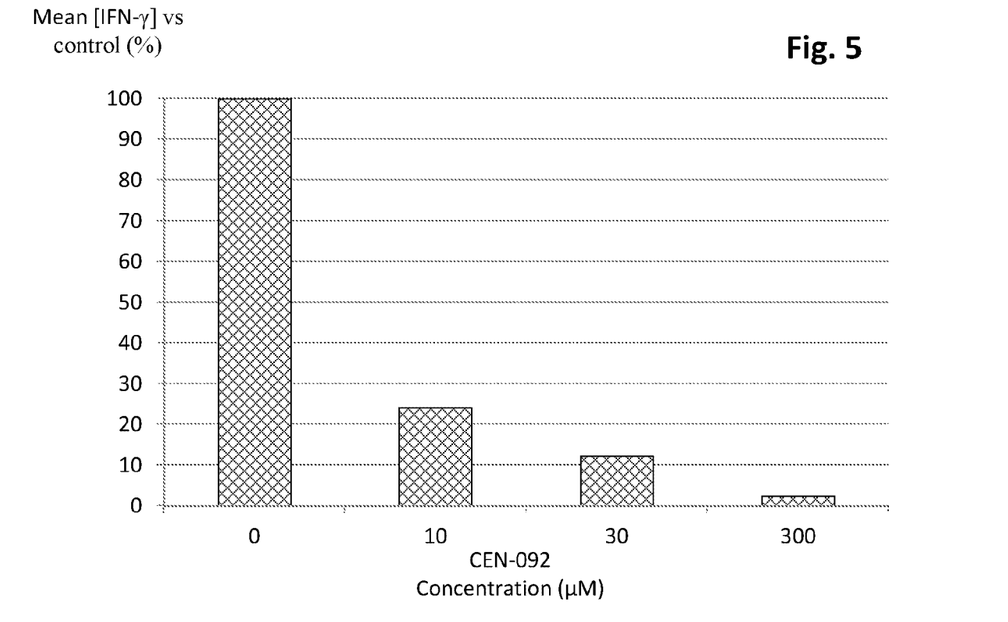
FIG. 5 is a chart showing the effects of compound CEN-092 on IFN-γ production in human peripheral blood mononuclear cells (PBMCs) based on the mean concentrations from Experiment 2.
Figure 6:
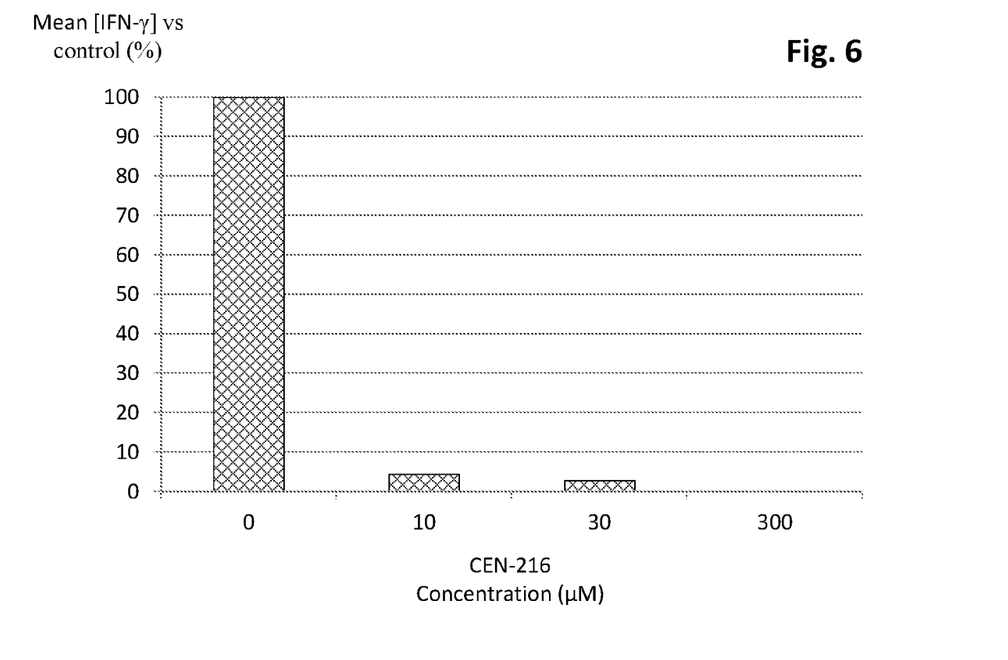
FIG. 6 is a chart showing the effects of compound CEN-216 on IFN-γ production in human peripheral blood mononuclear cells (PBMCs) based on the mean concentrations from Experiment 2.

These results are also illustrated in the charts in FIGS. 1 and 2. The error bars are based on the mean concentrations±SEM (standard error of mean).

Lamotrigine inhibits the amount of IFN-γ produced by the PBMCs, with a clear trend towards greater inhibition at increased lamotrigine concentrations, with statistically significant (P<0.05) reductions at concentrations of 10 to 100 μM.

Subject 3 showed the most pronounced reduction in IFN-γ production, with a 75% reduction observed when using 100 μM lamotrigine. To ensure that this result didn't affect the significance of the results from the other four subjects, the significance (Student's T-test) value was recalculated without including the results from subject 3. The results still confirmed a statistically significant (P<0.05) inhibition of IFN-γ production at 10, 30 and 100 μM lamotrigine. No significance value was calculated for the results using 300 μM lamotrigine, since the blood from only two of the subjects was tested. However, the data available show a continuing trend towards further increased inhibition at 300 μM.

Lamotrigine did not appear to alter PBMC viability.

Sipatrigine did not inhibit IFN-γ production. Although some variations appear to be observed, they are not statistically significant to a P<0.05 level.

There does not appear to be a correlation with calcium channel blocking activity, since lamotrigine and sipatrigine are both calcium channel inhibitors.

Experiment 2

A similar set of tests were carried out, in which three compounds known as CEN-079(3,5-diamino-6-[2-(3,4,5-trichlorothienyl)]-1,2,4-triazine), CEN-092(3,5-diamino-6-(3,5-bistrifluoromethylphenyl)-1,2,4-triazine) and CEN-216 (3,5-diamino-6-(2,3-dichlorophenyl)-2,3(2,5)-dihydro-3(5)-imino-2-(2,2,2-trichloroethyl)-1,2,4-triazine) were compared with lamotrigine. CEN-079, CEN-092 and CEN-216 are within the scope of Formulae 1, 2 and 3.

50 ml of blood from three healthy adult donors was collected by venepuncture in heparinised tubes. The blood samples where centrifuged at 3000 rpm for 15 minutes. The supernatant plasma was collected in a centrifuge tube, and centrifuged at 3000 rpm for a further 10 minutes. The supernatant was then collected in a plain tube, and stored at −70° C. for future use.

The cells from the first centrifuged heparinised tube were diluted 1:1 in RPMI-1640, and mixed by multiple inversions. The cell mixture was then slowly layered, using a sterile plastic 3 ml pipette, along a tube wall containing lymphoprep (Nycomed) at a ratio of 2:1 cells/RPMI-1640: Lymphoprep in a 25 ml universal tube. The mixture was centrifuged at 2400 rpm for 30 minutes, and left to stand for 20 minutes. PBMCs were slowly removed from the interface using a sterile plastic pipette, and collected in a 15 ml centrifuge tube.

The cells were washed twice by diluting in RPMI-1640 with 2 mM L-glutamine, 100 U/ml penicillin and 100 μg/ml streptomycin at a ratio of 1:1. The mixture was centrifuged at 3000 rpm for 15 minutes, and the supernatant decanted. PBMCs were then diluted in RPMI-1640 containing 2 mM L-glutamine, 100 U/ml penicillin and 100 μg streptomycin, to make up a volume of 6 ml for subjects 1 and 2, and 9 ml for subject 3.

Cells were counted using an Improved Neubauer haemocytometer (Hawksley, UK) on a light microscope. 10 μl of cell suspension was loaded onto the haemocytometer using a sterile plastic pipette. Cells were counted in five out of 25 1 mm squares, from which the total cell count was calculated.

Cell viability was determined by trypan blue exclusion, using an equal volume of cells and trypan blue.

5 μg/ml PHA was used as a T cell activating agent for the production of IFN-γ. The PBMCs were treated with the four test compounds (lamotrigine, CEN-079, CEN-092, CEN-216) at concentrations of 10 μM, 30 μM and 300 μM to assess their effects on IFN-γ production by the stimulated T cells.

The tests were carried out as for Experiment 1, in which $2×10^6$ PBMC/ml, 25 μl of 5% autologous plasma, and 2.63

µl of 5 µg/ml PHA were used. Test compound at each concentration was then added, except for one control case.

10 µM solutions were obtained by adding 1.05 µl of a 5 mM solution of the compounds to the above PBMC-containing solution. 30 µM solutions were obtained by adding 3.15 µl of the 5 mM solution of the compounds. 300 µM solutions were obtained by adding 3.15 µl of 50 mM solutions of the compounds.

The tubes were covered, gently shaken to mix the contents, and incubated for 24 hours at 37° C. The tubes were then centrifuged at 2500 rpm for 10 minutes. The supernatant was collected in a 3 ml plastic pipette, and aliquots were stored at −70° C. before being analysed.

Cell viability was assessed by trypan blue exclusion.

Quantitative measurement of IFN-γ was achieved in a similar way to Experiment 1, i.e. by enzyme-linked immunosorbent assay (ELISA, R&D Systems Europe Ltd). The test was performed according to the supplier's instructions. Donor samples were diluted 1:1 in phosphate buffered silane (PBS) and assayed simultaneously with IFN-γ standard samples, in duplicate. The standard curve ranged from 15.6 pg/ml to 1000 pg/ml.

A 96-well multiwell microplate (high binding Costar) was prepared, by diluting a capture antibody (720 µg/ml of mouse anti-human IFN-γ) in PBS to a working concentration of 4.0 µg/ml. 100 µl was immediately coated on each well, and left overnight at room temperature. The wells were washed three times in wash buffer, using microplate autowasher (LT-3000, LabTech International Ltd). The remainder of the wash buffer in the wells was removed by blotting on to clean paper towels. The plate was blocked by adding 300 µl Block buffer (1% BSA in PBS) to each well and incubated at room temperature for 1 hour. The plate was washed three further times as before. The standard (120 ng/ml recombinant human IFN-γ) was diluted in the reagent diluent (1% BSA, 0.05% Tween 20 in trisbuffered saline) in the concentration range 15.6 pg/ml-1000 pg/ml by 2-fold serial dilution.

After washing the plate three times, 100 µl of the standard, blank and stimulated PBMC supernatant were added in duplicate to the wells. The plate was covered in adhesive strip and incubated for 2 hours at room temperature. It was then washed three times as before, and 100 µl of detection antibody (9 µg/ml biotinylated goat anti-human IFN-γ reconstituted with 1 ml reagent diluent) was added to each well. The plate was sealed with adhesive strip and incubated for 2 hours at room temperature. The wells were then washed three times, and 100 µl per well of the working dilution of Streptavidin-HRP was added. The plate was incubated at room temperature away from direct light for 20 minutes.

The plate was then washed three times, and 100 µl substrate solution (1:1 $H_2O_2$:tetramethylbenzidine) was added to each well and incubated for 20 minutes at room temperature. 50 µl stop solution (2% $H_2SO_4$) was then added to each of the wells.

Absorbance at 450 nm of each well was determined using a microplate reader (MultiScan Ex, Thermo Lab Systems). Concentrations of IFN-γ in pg/ml were calculated based on a positive linear regression calculation of the absorbance results of the standards.

Cell viability of the three subjects was 94.4% or more before testing, and 87.1% or more after treatment with the test compounds.

Results of the performance of the compounds towards IFN-γ inhibition are shown in Table 2.

FIGS. 3 to 6 illustrate the results in the form of the averaged percentage of IFN-γ concentration versus control.

TABLE 2

Effects of Compounds on IFN-γ Production by PBMCs

| Compound | [IFN-γ] (pg/ml) | | | [IFN-γ] vs control (%) | | |
|---|---|---|---|---|---|---|
| | Subject 1 | Subject 2 | Subject 3 | Subject 1 | Subject 2 | Subject 3 |
| Control | 698.5 | 2026 | 2127.0 | | | |
| Lamotrigine | | | | | | |
| 10 µM | 732 | 1591.5 | 1590.0 | 104.7 | 78.6 | 74.8 |
| 30 µM | 454 | 1400.5 | 833.0 | 65 | 69.1 | 39.2 |
| 300 µM | 59.5 | 215.0 | 186.0 | 8.5 | 10.6 | 8.7 |
| CEN-079 | | | | | | |
| 10 µM | 154.5 | 757.5 | 611.5 | 22.1 | 36.9 | 28.7 |
| 30 µM | 53 | 178.5 | 41.5 | 7.60 | 1.80 | 2.0 |
| 300 µM | 0.00 | 0.0 | 0.0 | 0.0 | 0.0 | 0.0 |
| CEN-092 | | | | | | |
| 10 µM | 112.5 | 728.5 | 423.5 | 16.1 | 36.0 | 19.9 |
| 30 µM | 52.0 | 499.0 | 91.5 | 7.4 | 24.6 | 4.3 |
| 300 µM | 0.00 | 0.0 | 146.0 | 0.0 | 0.0 | 6.9 |
| CEN-216 | | | | | | |
| 10 µM | 0.00 | 187.0 | 82.0 | 0.0 | 9.2 | 3.9 |
| 30 µM | 0.00 | 59.0 | 122.0 | 0.0 | 2.9 | 5.7 |
| 300 µM | 0.00 | 0.0 | 0.0 | 0.0 | 0.0 | 0.0 |

Table 3 below also shows the $IC_{50}$ (concentration to inhibit IFN-γ production by 50%) values for lamotrigine, CEN-079 and CEN-092. These data confirm that much less (lower concentrations of) CEN-079 and CEN-092 is required to inhibit IFN-γ production compared to lamotrigine.

TABLE 3

$IC_{50}$ values

| Compound | $IC_{50}$ (µM) |
|---|---|
| Lamotrigine | 43 |
| CEN-079 | 6 |
| CEN-092 | 3 |

As before, lamotrigine is shown to be an inhibitor of IFN-γ production in PBMCs. However, CEN-079, CEN-092 and CEN-216 are shown to be significantly more effective inhibitors compared to lamotrigine. It therefore appears that these compounds could act as potential candidates for treating diseases or medical conditions that are treatable or controllable by inhibiting IFN-γ.

The invention claimed is:

1. A method of treating or controlling medical conditions and diseases that are treatable or controllable by inhibiting IFN-γ production, wherein said medical conditions and diseases are selected from prion diseases, rheumatoid arthritis, inflammatory bowel disease, autoimmune skin diseases, psoriasis, Sjögren's syndrome, Crohn's disease, and type 1 diabetes mellitus, comprising:

administering to a patient a therapeutically effective amount of a compound of Formula 1, Formula 2 or Formula 3 or a solvate, tautomer, or pharmaceutically acceptable salt thereof, for use in the treatment or control of medical conditions and diseases that are treatable or controllable by inhibiting interferon gamma (IFN-γ) production Formula 1

Formula 2

Formula 3 in which:

A is selected from:
- i. a phenyl ring substituted with up to five substituents, each independently selected from halogen atoms, haloalkyl groups having from 1 to 4 carbon atoms, alkoxy groups having from 1 to 4 carbon atoms, and haloalkoxy groups having from 1 to 4 carbon atoms; and
- ii. a thiophene ring optionally substituted with up to three substituents each selected independently from halogen atoms, alkyl groups having from 1 to 4 carbon atoms, haloalkyl groups having from 1 to 4 carbon atoms, alkoxy groups having from 1 to 4 carbon atoms and haloalkoxy groups having from 1 to 4 carbon atoms; and
- iii. a $C(R^d)_3$ group, wherein each $R^d$ is independently selected from hydrogen, alkyl groups having from 1 to 4 carbon atoms, haloalkyl groups having from 1 to 4 carbon atoms, alkoxy groups having from 1 to 4 carbon atoms, haloalkoxy groups having from 1 to 4 carbon atoms, and phenyl rings optionally substituted with up to five substituents, each independently selected from halogen atoms, alkyl groups having from 1 to 4 carbon atoms, haloalkyl groups having from 1 to 4 carbon atoms, alkoxy groups having from 1 to 4 carbon atoms, and haloalkoxy groups having from 1 to 4 carbon atoms, and wherein at least one R groups is an optionally substituted phenyl ring;

$R^a$ is selected from hydrogen, haloalkyl groups having from 1 to 4 carbon atoms, and alkyl-alkoxy groups having from 1 to 6 carbon atoms that are optionally substituted with one or more halogen atoms, with the proviso that when A is a phenyl ring comprising one or more directly bound halogen substituents, the compound is of Formula 2 or 3, and $R^a$ is not hydrogen;

each $R^b$ is independently selected from hydrogen, alkyl groups having from 1 to 4 carbon atoms, and haloalkyl groups having from 1 to 4 carbon atoms.

2. The method according to claim 1, in which group A is an aromatic ring comprising at least one halogen, haloalkyl or haloalkoxy substituent.

3. The method according to claim 1, in which the compound is of Formula 4, Formula 5 or Formula 6, or a solvate, tautomer or pharmaceutically acceptable salt thereof:

Formula 4

Formula 5

Formula 6 wherein:

n is an integer from 1 to 5;

$R^a$ and $R^b$ are as defined in claim 1; and each $R^c$ is independently selected from haloalkyl groups having from 1 to 4 carbon atoms, alkoxy groups having from 1 to 4 carbon atoms, and haloalkoxy groups having from 1 to 4 carbon atoms.

4. The method according to claim 3, in which n is 2.

5. The method according to claim 3, in which all $R^c$ substituents are selected from haloalkyl groups.

6. The method according to claim 5, in which the haloalkyl groups are fluoromethyl groups.

7. The method according to claim 3, in which the compound is of Formula 4, or $R^a$ is hydrogen.

8. The method according to claim 1, in which the compound is of Formula 5 or 6, or a solvate, tautomer, or pharmaceutically acceptable salt thereof:

Formula 5

Formula 6 wherein:

n is an integer from 1 to 5;

$R^a$ is selected from haloalkyl groups having from 1 to 4 carbon atoms, and alkyl-alkoxy groups having from 1 to 6 carbon atoms that are optionally substituted with one or more halogen atoms;

R$^b$ is as defined in claim 1; and at least one R$^c$ is a halogen atom, and wherein each additional R$^c$ is independently selected from halogen atoms, haloalkyl groups having from 1 to 4 carbon atoms, alkoxy groups having from 1 to 4 carbon atoms, and haloalkoxy groups having from 1 to 4 carbon atoms.

9. The method according to claim 8, in which all R$^c$ are halogen atoms.

10. The method according to claim 9, in which R$^a$ is selected from haloalkyls.

11. The method according to claim 1, in which the compound is of Formula 7, Formula 8, Formula 9, Formula 10, Formula 11 or Formula 12, or a solvate, tautomer or salt thereof:

wherein:

n is an integer from 1 to 3;

R$^a$ and R$^b$ are as defined in claim 1; and each R$^c$ is independently selected from halogen atoms, alkyl groups having from 1 to 4 carbon atoms, haloalkyl groups having from 1 to 4 carbon atoms, alkoxy groups having from 1 to 4 carbon atoms, and haloalkoxy groups having from 1 to 4 carbon atoms.

12. The method according to claim 11, in which all R$^c$ substituents are halogen atoms.

13. The method according to claim 11, in which the compound is of Formula 7, or R$^a$ is hydrogen.

14. The method according to claim 1, in which the ring A is selected from:

2,5-bistrifluoromethylphenyl;
3,5-bistrifluoromethylphenyl;
3,4,5-trimethoxyphenyl;
2-difluoromethoxyphenyl;
2-trifluoromethoxyphenyl;
2-(1,1,2,2-tetrafluoroethoxy)phenyl;
3-(1,1,2,2-tetrafluoroethoxy)phenyl;
2,5-bis(2,2,2-trifluoroethoxy)phenyl;
3,5-bis(2,2,2-trifluoroethoxy)phenyl;
2,3,4-trifluorophenyl;
2,3,4,5-tetrafluorophenyl;
2,3,4,5,6-pentafluorophenyl;
2,3-dichlorophenyl;
2,5-dichlorophenyl;
3,5-dichlorophenyl;
2,6-dichlorophenyl;
2,3,5-trichlorophenyl;
2,3,6-trichlorophenyl;
2-bromophenyl;
3-bromophenyl;
2-fluoro-3-chloro-5-trifluoromethylphenyl;
2-chloro-4,5-difluorophenyl;
2-chloro-3-trifluoromethylphenyl;
3-chloro-5-trifluoromethylphenyl;
5-chloro-2-trifluoromethylphenyl; and
2,3-dichloro-6-trifluoromethylphenyl
5-chlorothienyl;
2,5-dichlorothienyl;
3,4,5-trichlorothienyl;
3-bromothienyl;
5-bromothienyl; and
4,5-dibromothienyl.

15. The method according to claim 1, in which all occurrences of R$^b$ are hydrogen.

16. The method according to claim 1, in which the compound is selected from:

3,5-diamino-6-(2,5-bistrifluoromethylphenyl)-1,2,4-triazine [CEN-198]
3,5-diamino-6-(3,5-bistrifluoromethylphenyl)-1,2,4-triazine [CEN-092]
3,5-diamino-6-(3,4-dimethoxyphenyl)-1,2,4-triazine [CEN-115]
3,5-diamino-6-(3,5-dimethoxyphenyl)-1,2,4-triazine [CEN-192]
3,5-diamino-6-(3,4,5-trimethoxyphenyl)-1,2,4-triazine [CEN-095]
3,5-diamino-6-(2-difluoromethoxyphenyl)-1,2,4-triazine [CEN-142]
3,5-diamino-6-(2-trifluoromethoxyphenyl)-1,2,4-triazine [CEN-056]
3,5-diamino-6-[3-(1,1,2,2-tetrafluoroethoxy)phenyl]-1,2,4-triazine [CEN-108]
3,5-diamino-6-[2-(1,1,2,2-tetrafluoroethoxy)phenyl]-1,2,4-triazine [CEN-137]
3,5-diamino-6-[2,5-bis(2,2,2-trifluoroethoxy)phenyl]-1,2,4-triazine [CEN-140]
3,5-diamino-6-[3,5-bis(2,2,2-trifluoroethoxy)phenyl]-1,2,4-triazine [CEN-193]

5(3)-amino-6-(2,3-dichlorophenyl)-2,3(2,5)-dihydro-3(5)-imino-2-(2-fluoroethyl)-1,2,4-triazine
5(3)-amino-6-(2,3-dichlorophenyl)-2,3(2,5)-dihydro-3(5)-imino-2-(2,2-difluoroethyl)-1,2,4-triazine
5(3)-amino-6-(2,3-dichlorophenyl)-2,3(2,5)-dihydro-3(5)-imino-2-(2,2,2-trifluoroethyl)-1,2,4-triazine [CEN-067]
5-amino-6-(2,3-dichlorophenyl)-2,3-dihydro-3-imino-2-(3,3,3-trifluoropropyl)-1,2,4-triazine
5(3)-Amino-6-(2,3-dichlorophenyl)-2,3(2,5)-dihydro-3(5)-imino-2-(2,2,3,3-tetrafluoropropyl)-1,2,4-triazine [CEN-218]
5(3)-Amino-6-(2,3-dichlorophenyl)-2,3(2,5)-dihydro-3(5)-imino-2-(2,2,3,3,3-pentafluoropropyl)-1,2,4-triazine [CEN-217]
5(3)-Amino-6-(2,3-dichlorophenyl)-2,3(2,5)-dihydro-3(5)-imino-2-(2,2,2-trichloroethyl)-1,2,4-triazine [CEN-216]
5(3)-amino-6-(2,3,-dichlorophenyl)-2,3(2,5)-dihydro-3(5)-imino-2-(2-isopropoxy)ethyl-1,2,4-triazine [CEN-091]
5(3)-amino-6-(2,3,5-trichlorophenyl)-2,3(2,5)-dihydro-3(5)-imino-2-(2-fluoroethyl)-1,2,4-triazine
5(3)-amino-6-(2,3,5-trichlorophenyl)-2,3(2,5)-dihydro-3(5)-imino-2-(2,2-difluoroethyl)-1,2,4-triazine [CEN-085]
5(3)-amino-6-(2,3,5-trichlorophenyl)-2,3(2,5)-dihydro-3(5)-imino-2-(3,3,3-trifluoropropyl)-1,2,4-triazine
5(3)-amino-6-(2,3,5-trichlorophenyl)-2,3(2,5)-dihydro-3(5)-imino-2-(2,2,2-trichloroethyl)-1,2,4-triazine [CEN-248]
5(3)-Amino-6-(3-chloro-2-fluoro-5-trifluoromethyphenyl)-2,3(2,5)-dihydro-3(5)-imino-2-(2,2,3,3-tetrafluoropropyl)-1,2,4-triazine [CEN-210]
5(3)-Amino-6-(3-chloro-2-fluoro-5-trifluoromethyphenyl)-2,3(2,5)-dihydro-3(5)-imino-2-(2,2,3,3,3-pentafluoropropyl)-1,2,4-triazine [CEN-211]
3,5-diamino-6-[2-(5-chlorothienyl)]-1,2,4-triazine [CEN-138]
3,5-diamino-6-[3-(2,5-dichlorothienyl)]-1,2,4-triazine [CEN-071]
3,5-diamino-6-[2-(3,4,5-trichlorothienyl)]-1,2,4-triazine [CEN-079]
3,5-diamino-6-[2-(5-bromothienyl)]-1,2,4-triazine [CEN-124]
3,5-diamino-6-[2-(3-bromothienyl)]-1,2,4-triazine [CEN-125]
3,5-diamino-6-[2-(4,5-dibromothienyl)]-1,2,4-triazine [CEN-122]
3,5-Diamino-6-(diphenylmethyl)-1,2,4-triazine [CEN-130]
3,5-Diamino-6-(1,1-diphenylethyl)-1,2,4-triazine [CEN-147]
5(3)-Amino-6-(1,1-diphenylethyl)-2,3(2,5)-dihydro-3(5)-imino-2-methyl-1,2,4-triazine [CEN-149]
3,5-Diamino-6-(triphenylmethyl)-1,2,4-triazine [R3=R4=R5=Ph] [CEN-153]
3,5-Diamino-6-(1-cyclopentyl-1-phenylmethyl)-1,2,4-triazine [CEN-163]
3,5-Diamino-6-(1-isopropyl-1-phenylmethy)-1,2,4-triazine [CEN-201]; and
3,5-Diamino-6-[1,1 bis-(4-chlorophenyl)methyl]-1,2,4-triazine [CEN-213]

and solvates, tautomers and pharmaceutically acceptable salts thereof.

17. The method according to claim 16, in which the compound is selected from:
3,5-diamino-6-[2-(3,4,5-trichlorothienyl)]-1,2,4-triazine [CEN-079];
3,5-diamino-6-(3,5-bistrifluoromethylphenyl)-1,2,4-triazine [CEN-092]; and
5(3)-Amino-6-(2,3-dichlorophenyl)-2,3(2,5)-dihydro-3(5)-imino-2-(2,2,2-trichloroethyl)-1,2,4-triazine [CEN-216]

and solvates, tautomers and pharmaceutically acceptable salts thereof.

18. The method according to claim 1, in which the compound is of Formula 13, Formula 14 or Formula 15, or a solvate, tautomer or salt thereof:

Formula 13

Formula 14

Formula 15 wherein:
$R^b$ is as defined in claim 1;
each $R^d$ is independently selected from hydrogen, alkyl groups having from 1 to 4 carbon atoms, haloalkyl groups having from 1 to 4 carbon atoms, alkoxy groups having from 1 to 4 carbon atoms, haloalkoxy groups having from 1 to 4 carbon atoms, and
phenyl rings optionally substituted with up to five $R^c$ substituents,
n is from 0 to 5, and
each $R^c$ is independently selected from halogen atoms, alkyl groups having from 1 to 4 carbon atoms, haloalkyl groups having from 1 to 4 carbon atoms, alkoxy groups having from 1 to 4 carbon atoms, and haloalkoxy groups having from 1 to 4 carbon atoms.

* * * * *